United States Patent
Bey et al.

(10) Patent No.: US 11,766,653 B2
(45) Date of Patent: Sep. 26, 2023

(54) METHOD FOR CARRYING OUT A GAS/FLUID TWO-PHASE HIGH-PRESSURE REACTION

(71) Applicant: BASF SE, Ludwigshafen am Rhein (DE)

(72) Inventors: Oliver Bey, Ludwigshafen am Rhein (DE); Peter Zehner, Weisenheim am Berg (DE); Andreas Keller, Ludwigshafen am Rhein (DE); Stephanie Renz, Ludwigshafen am Rhein (DE); Mathias Schelwies, Ludwigshafen am Rhein (DE); Rocco Paciello, Ludwigshafen am Rhein (DE); Martin Haubner, Ludwigshafen am Rhein (DE); Guenter Wegner, Ludwigshafen am Rhein (DE); Gerd Tebben, Ludwigshafen am Rhein (DE); Gunnar Heydrich, Ludwigshafen am Rhein (DE); Georg Seeber, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 337 days.

(21) Appl. No.: 17/274,110

(22) PCT Filed: Sep. 3, 2019

(86) PCT No.: PCT/EP2019/073484
§ 371 (c)(1),
(2) Date: Mar. 5, 2021

(87) PCT Pub. No.: WO2020/048998
PCT Pub. Date: Mar. 12, 2020

(65) Prior Publication Data
US 2021/0354101 A1    Nov. 18, 2021

(30) Foreign Application Priority Data
Sep. 5, 2018 (EP) .................................. 18192743

(51) Int. Cl.
*C07C 45/62* (2006.01)
*B01J 10/00* (2006.01)
(Continued)

(52) U.S. Cl.
CPC ............. *B01J 10/002* (2013.01); *B01J 3/02* (2013.01); *B01J 3/042* (2013.01); *B01J 4/002* (2013.01);
(Continued)

(58) Field of Classification Search
CPC ........... C07C 45/62; B01J 10/002; B01J 3/02; C07B 53/00
See application file for complete search history.

(56) References Cited

U.S. PATENT DOCUMENTS

2018/0057437 A1    3/2018    Schelwies et al.

FOREIGN PATENT DOCUMENTS

| EP | 1231198 A1 | 8/2002 |
| EP | 1338333 A1 | 8/2003 |

(Continued)

OTHER PUBLICATIONS

International Preliminary Report on Patentability received for PCT Patent Application No. PCT/EP2019/073484, dated Mar. 18, 2021, 16 pages (9 pages of English Translation and 7 pages of Original Document).

(Continued)

*Primary Examiner* — Sikarl A Witherspoon
(74) *Attorney, Agent, or Firm* — Faegre Drinker Biddle & Reath LLP (57) ABSTRACT

A process for performing a continuous gas/liquid biphasic high-pressure reaction, wherein a gas and a liquid are introduced into a backmixed zone of a reactor and in the backmixed zone the gas is dispersed in the liquid by stirring, injection of gas and/or a liquid jet, a reaction mixture consecutively traverses the backmixed zone and a zone of limited backmixing, and a liquid reaction product is withdrawn at a reaction product outlet of the zone of limited backmixing, wherein the reactor comprises: an interior formed by a cylindrical vertically oriented elongate shell, a bottom and a cap, wherein the interior is divided by means of internals into the backmixed zone, the zone of limited backmixing and a cavity, a first cylindrical internal element which in the interior extends in the longitudinal direction of the reactor and which delimits the zone of limited backmixing from the backmixed zone, backmixing-preventing second internal elements in the form of random packings, structured packings or liquid-permeable trays arranged in the zone of limited backmixing and a third internal element which in the interior extends in the longitudinal direction of the reactor and is open at the bottom, wherein the third internal element forms the cavity in which gas bubbles collect and do not escape upwards, thus preventing the volume of the cavity from being occupied by liquid and reducing the reaction volume. The reaction volume of the reactor used in the process can be reversibly reduced in simple fashion. The invention further relates to a process for adapting the reaction volume of a reactor suitable for performing a gas/liquid biphasic high-pressure reaction having an outlet for a liquid reaction product in which an internal element is arranged so as to form a cavity open at the bottom in which gas bubbles collect and do not escape upwards, thus preventing the volume of the cavity from being occupied by liquid and reducing the reaction volume.

15 Claims, 2 Drawing Sheets

(51) Int. Cl.
*B01J 13/02* (2006.01)
*B01J 3/02* (2006.01)
*B01J 3/04* (2006.01)
*B01J 4/00* (2006.01)
*B01J 31/24* (2006.01)
*C07B 53/00* (2006.01)

(52) U.S. Cl.
CPC ........... *B01J 31/2409* (2013.01); *C07C 45/62* (2013.01); *B01J 2203/065* (2013.01); *B01J 2531/822* (2013.01); *C07B 53/00* (2013.01)

(56) References Cited

FOREIGN PATENT DOCUMENTS

| | | |
|---|---|---|
| EP | 2676928 A1 | 12/2013 |
| WO | 2006/040096 A1 | 4/2006 |
| WO | 2008/132057 A1 | 11/2008 |
| WO | 2009/153123 A1 | 12/2009 |
| WO | 2016/097242 A1 | 6/2016 |

OTHER PUBLICATIONS

International Search Report and Written Opinion received for PCT Patent Application No. PCT/EP2019/073484, dated Nov. 18, 2019, 19 pages. (9 pages of English Translation and 10 pages of Original Document).

METHOD FOR CARRYING OUT A GAS/FLUID TWO-PHASE HIGH-PRESSURE REACTION

CROSS-REFERENCE TO RELATED APPLICATIONS

This application is a national stage application (under 35 U.S.C. § 371) of PCT/EP2019/073484, filed Sep. 3, 2019, which claims benefit of European Application No. 18192743.5, filed Sep. 5, 2018, both of which are incorporated herein by reference in their entirety.

The invention relates to a process for performing a gas/liquid biphasic high-pressure reaction. The invention further relates to a process for adapting the reaction volume of a reactor suitable for performing a gas/liquid biphasic high-pressure reaction.

Numerous conversions are performed under elevated pressure in a pressure reactor. For example the hydrogenation of organic compounds makes use of the reaction of a hydrogenatable compound with gaseous hydrogen. It is known to perform the hydrogenation in a first backmixed zone and a second zone with limited backmixing. The backmixing in the first zone allows advantageous removal of reaction heat while the second zone is used for completion of the reaction conversion.

WO 2009/153123 describes a continuous process for hydrogenation of organic compounds in a multiphasic system in the presence of a homogeneous or heterogeneous catalyst wherein the process is performed in two stages, wherein the first stage is performed in a loop reactor having an external heat exchanger and the second stage is performed in a bubble column reactor with limited backmixing.

EP 1 338 333 A1 describes a reactor cascade composed of a sealed main reactor and a sealed postreactor, wherein the postreactor is located inside the main reactor vessel.

EP 1 231 198 A1 describes a continuous process for hydroformylation of olefins which employs a reactor comprising two consecutively traversable reaction spaces, wherein the second reaction space may comprise perforated plates.

In the case of continuously operating reactors there is at any time a volume flow being introduced into the reactor and a volume flow being withdrawn again at the reactor outlet. When the introduced volume flow is constant over time the average residence time of the reaction mixture in the reactor is also constant. The average residence time is a measure of the average amount of time required for the reaction mixture to traverse the reactor. When the volume flow is non-constant over time, for instance in the case of varying generation of a starting material and/or varying need for a reaction product, the average residence time also changes. In many cases an excessively long residence of the reaction mixture in the reactor is unwanted, for instance because unwanted subsequent reactions and/or decompositions may occur. In these cases it is desirable to be able to reversibly reduce the reaction volume of the reactor in a simple fashion, in particular in the case of reactions that are carried out in the presence of a gas phase but where the actual conversion is carried out in the liquid phase.

Reversible reduction of the reaction volume of the reactor may be achieved by introducing displacement bodies, which are solid or sealed on all sides, into the reactor. When these displacement bodies have inner cavities the bodies must be configured so as to be pressure resistant toward the reaction pressure. A simpler, cost-effective solution is desirable.

The object is achieved by a process for performing a gas/liquid biphasic high-pressure reaction, wherein a gas and a liquid are introduced into a backmixed zone of a reactor and in the backmixed zone the gas is dispersed in the liquid by stirring and/or injection of gas and/or a liquid jet, a reaction mixture consecutively traverses the backmixed zone and a zone of limited backmixing, and a liquid reaction product is withdrawn at a reaction product outlet of the zone of limited backmixing, wherein the reactor comprises:

an interior formed by a cylindrical vertically oriented elongate shell, a bottom and a cap, wherein the interior is divided by means of internals into the backmixed zone, the zone of limited backmixing and a cavity, a first cylindrical internal element which in the interior extends in the longitudinal direction of the reactor and which delimits the zone of limited backmixing from the backmixed zone, backmixing-preventing second internal elements in the form of random packings, structured packings or liquid-permeable trays arranged in the zone of limited backmixing and a third internal element which in the interior extends in the longitudinal direction of the reactor, is open at the bottom and is preferably delimited at the top by the first cylindrical internal element, wherein the third internal element forms the cavity in which gas bubbles collect and do not escape upwards, thus preventing the volume of the cavity from being occupied by liquid and reducing the reaction volume.

A high-pressure reaction is to be understood as meaning a reaction performed at a pressure elevated with respect to ambient pressure, for example at at least 5 bar absolute, at least 20 bar absolute or at least 50 bar absolute.

The reactor comprises an interior formed by a cylindrical, vertically oriented elongate shell, a bottom and a cap. The ratio of the length to diameter of the shell is typically 2:1 to 100:1, preferably 5:1 to 100:1, particularly preferably 5:1 to 50:1, very particularly preferably 5:1 to 30:1.

The interior of the reactor is divided by means of internals into a backmixed zone, a zone of limited backmixing and a cavity. The backmixed zone and the zone of limited backmixing are consecutively traversable by the reaction mixture. A first cylindrical internal element in the interior extends in the longitudinal direction of the reactor and delimits the zone of limited backmixing from the backmixed zone.

A third internal element which in the interior extends in the longitudinal direction of the reactor forms a cavity open at the bottom. Gas bubbles collect in the cavity and cannot escape upwards. When the cavity is completely filled with gas the volume of the cavity can no longer be occupied by liquid. The reaction volume is reduced and the average residence time of the reaction mixture is shortened. In one embodiment the third internal element comprises a fluid outlet, in particular a gas outlet, by means of which the gas volume in the cavity may be adjusted.

In contrast to hollow displacement bodies which are sealed on all sides, the third internal element need not be configured so as to be pressure resistant. It may be manufactured from a metal sheet, for example. The third internal element is preferably a cylindrical internal element so that the cavity has a circular horizontal cross section. In one embodiment the cylindrical internal element is arranged concentrically to the shell.

It is preferable when the third internal element is arranged such that its lower end has a distance from the bottom which is in the range from 10% to 30%, particularly preferably 10% to 20% and very particularly preferably 10% to 15% of the height of the shell.

It is preferable when the volume ratio of the backmixed zone to the zone of limited backmixing is in the range from 0.25:1 to 4:1, particularly preferably in the range from 0.3:1 to 3:1.

It is preferable when the volume ratio of the backmixed zone to the cavity is in the range from 0.5:1 to 10:1, particularly preferably in the range from 1:1 to 5:1.

It is preferable when the volume ratio of the backmixed zone to the gas space is in the range from 1:1 to 30:1, particularly preferably in the range from 3:1 to 10:1.

A reactor having volume ratios in this range allows optimal utilization of the reactor space.

When a gas/liquid biphasic high-pressure reaction is performed in the reactor, gas collects in the upper portion of the backmixed zone and forms a gas phase while the lower portion of the backmixed zone contains a liquid phase.

In the backmixed zone the gas is dispersed in the liquid by stirring, injection of gas and/or a liquid jet.

Suitable means for stirring comprise all stirrers familiar to those skilled in the art, such as propeller stirrers.

Injection of gas in the liquid is carried out via a gas nozzle arranged below the liquid level.

A jet nozzle generates a liquid jet allowing dispersion of the gas phase and commixing within the backmixed zone.

Gas and liquid are preferably introduced via a jet nozzle. The jet nozzle is especially in the form of a two-fluid nozzle. In the case of two-fluid nozzles the gas is supplied to the backmixed zone and dispersed with the liquid.

Supplying gas and liquid via a jet nozzle for gas and liquid may be carried out at any desired point in the backmixed zone, in particular an injection nozzle arranged below the liquid level. In a preferred embodiment the gas and the liquid are metered upwards into the backmixed zone via a two-fluid jet nozzle located in the bottom of the reactor.

The backmixed zone is suitably configured as an ascending jet reactor which via punctate or linear fluid injection allows large-scale recirculation of the contents of the backmixed zone. In order to achieve undisturbed large-scale circulation the backmixed zone is preferably substantially free from internals such as baffles, stirrers and the like.

The backmixed zone is preferably configured as a loop reactor. Examples of loop reactors are tubular reactors having internal and external loops. Such reactors are more particularly described for example in Ullmanns Encyclopedia (Ullmann's Encyclopedia of Industrial Chemistry, Verlag Chemie, Electronic Release 2008, 7th Edition, Chapters "Stirred Tank and Loop Reactors" and "Bubble Columns").

The loop reactor generally has an external circuit (external loops). A loop reactor having an external circuit generally has a takeoff at any desired point in the backmixed zone, preferably in the lower region of the backmixed zone, through which the reaction mixture is in an external circuit returned to the means for introducing gas and liquid using a conveying apparatus. The conveying apparatus is preferably a pump and the external circuit is therefore typically referred to as a pumped circulation circuit.

Examples of pumps are centrifugal pumps or rotary piston pumps, such as rotary lobe pumps, rotary vane pumps, circumferential piston pumps or gear pumps. It is particularly preferable to employ centrifugal pumps as the conveying apparatus.

It is preferable when the external circuit of the loop reactor comprises a heat exchanger. In the context of the present invention a thus-configured loop reactor is referred to as a loop reactor with external heat exchanger.

The heat exchanger is for example a tube bundle heat exchanger, double tube heat exchanger, plate heat exchanger or spiral heat exchanger. At reactor design pressures below 100 bar it is preferable to use a tube bundle heat exchanger while at higher pressures it is preferable to use one or more double tube heat exchangers connected in series.

In this case, the loop reactor with external heat exchanger is typically operated such that a portion of the reaction mixture from the backmixed zone is conveyed through the external pumped circulation circuit comprising the external heat exchanger, thus cooling the reaction mixture conveyed through the heat exchanger. The reaction mixture is finally returned to the backmixed zone using the means for introducing gas and liquid. The external pumped circulation generally vigorously commixes and recirculates the reaction mixture in the first reaction stage so that the residence time in the first stage typically corresponds to that of a fully backmixed stirred tank (CSTR). Typically, fresh gas and fresh liquid are introduced into the pumped circulation circuit and together with the stream already present in the pumped circulation circuit supplied to the backmixed zone as reaction mixture.

The backmixed zone has a gas outlet. Unconverted gas may be withdrawn via said outlet. The gas outlet is preferably located at the upper end of the cylindrical shell. The reactor is advantageously configured such that the withdrawn unconverted gas may be at least partially reintroduced into the reaction mixture in the backmixed zone via the means for introducing gas and liquid. To this end the unconverted gas from the gas outlet may be passed to the means for introducing gas and liquid via an external gas conduit.

In one embodiment when the liquid has a propensity for foaming the reactor comprises at least one fourth internal element which is arranged in the upper half of the backmixed zone and has a surface which promotes coalescence of foaming media. Suitable internal elements which promote coalescence of foaming media comprise elements for chemical, thermal or mechanical foam destruction. An overview is provided by Pahl et al. in Chem.-Ing.-Tech. 67 (1995), 300-312. In one embodiment the reactor comprises mechanical foam destruction measures, for example rotating elements or internals for sprinkling with autogenous liquid.

Any foam generated typically has the result that the boundary between the liquid phase and the gas phase in the backmixed zone is not clearly definable. The reactor therefore preferably comprises a riser tube whose lower end is arranged within the backmixed zone and whose upper end opens into the zone of limited backmixing so that liquid from the backmixed zone can ascend into the zone of limited backmixing via the riser tube. The riser tube is arranged such that its lower end is immersed in the liquid phase during the gas/liquid biphasic high-pressure reaction. The riser tube is suitably immersed into the liquid to such a depth that substantially no foam can penetrate into the riser tube. This substantially avoids contamination of downstream workup steps or subsequent reactions with foam.

The lower end of the riser tube is arranged at a distance from the bottom. During operation, the lower end of the riser tube has a distance from the bottom which is in the range from 10% to 95%, particularly preferably 30% to 90% and very particularly preferably 70% to 80% of the height of the liquid level.

The riser tube typically has a diameter in the range from 1% to 90%, preferably 2% to 50%, very particularly preferably 5% to 20%, of the diameter of the zone of limited backmixing.

The reactor preferably comprises a fifth internal element arranged at the lower end of the riser tube which substantially prevents entry of gas into the riser tube. In particular, the shape and arrangement of the fifth internal element substantially prevent gas bubbles ascending in the reaction mixture from entering the riser tube. The fifth internal element is preferably selected from a deflection weir and a U-tube, particularly preferably a deflection weir.

The backmixed zone is preferably at a higher pressure than the reaction product outlet in order to overcome the hydrostatic pressure in the zone of limited backmixing and the pressure drop generated upon traversal of the backmixing-preventing second internal elements. The higher pressure in the backmixed zone causes liquid to ascend from the backmixed zone into the zone of limited backmixing. The first cylindrical internal element and the backmixing-preventing second internal elements must be configured according to this differential pressure.

The backmixing in the zone of limited backmixing is limited by backmixing-preventing second internal elements. The installation of such apparatuses generally limits the circulation and thus the backmixing of gas and liquid. The residence time distribution in the zone of limited backmixing approximates that of a tubular reactor. This defined liquid residence time ensures that a high conversion in the high-pressure reaction is achieved.

The proportion of the gas phase in the reaction mixture in the zone of limited backmixing is preferably reduced compared to the backmixed zone. This effect may be achieved for example through the use of a riser tube and optionally a fifth internal element which substantially prevents entry of gas into the riser tube. Reducing a discrete gas phase in the zone of limited backmixing makes it possible to increase the liquid holdup in the zone of limited backmixing and increase the residence time of the liquid phase in the zone of limited backmixing. Since high-pressure reactions are carried out substantially in the liquid phase the reaction space is thus optimally utilized.

The limiting of backmixing in the zone of limited backmixing may be realized through installation of various internals. In one preferred embodiment the limiting of backmixing is effected through installation of a plurality of fixedly arranged trays in the zone of limited backmixing. This forms individual segments ("compartments") having defined reaction volumes between the individual trays. Each of the individual segments generally acts as an individual, backmixed stirred tank reactor. An increasing number of consecutive individual segments generally causes the residence time distribution of such a cascade to approach the residence time of a tubular reactor. The number of the thus-formed individual segments is preferably 2 to 20, particularly preferably 2 to 10, especially preferably 3 to 6. The volume of the individual segments formed is typically substantially identical. The trays are preferably liquid-permeable trays. It is particularly preferable when the trays are perforated plates.

In a further embodiment the limiting of backmixing is effected through installation of random packings. The random packings may have different shapes and are usually about 2 to 15 mm in size. Known examples include spherical and cylindrical solid bodies, Raschig rings (a hollow cylinder), Pall rings, Hiflow rings, Intalox saddles and the like. The random packings are preferably solid bodies. The random packings may be introduced into the zone of limited backmixing in ordered or disordered form (as a dumped bed). Materials that may be employed include glass, ceramic, metal and plastics.

In a further embodiment the limiting of backmixing is effected through incorporation of structured packings. Structured packings are a further development of ordered random packings. They have a regular structure. There are various designs of packings, such as woven or sheet metal packings. Materials that may be employed include metal, plastic, glass and ceramic.

The first internal element is preferably arranged concentrically to the shell so that the zone of limited backmixing has a circular horizontal cross section. The ratio of length to diameter of the zone of limited backmixing is typically 2:1 to 100:1, preferably 5:1 to 50:1, particularly preferably 7:1 to 25:1.

In the process according to the invention for performing a continuous gas/liquid biphasic high-pressure reaction a gas and a liquid are introduced into the backmixed zone in a reactor as described hereinabove, liquid is allowed to ascend from the backmixed zone into the zone of limited backmixing, preferably through a riser tube, unconverted gas is at least partially discharged via the gas outlet and a reaction product is withdrawn from the reaction product outlet.

It is preferable when the unconverted gas is at least partially reintroduced via an injection nozzle into the reaction mixture in the backmixed zone, for example via an external gas conduit.

In one embodiment the process is a process for preforming a homogeneous rhodium hydrogenation catalyst comprising at least one CO ligand. A process for pretreatment with a gas mixture comprising carbon monoxide and hydrogen is thus concerned.

It is preferable when the liquid comprises a dissolved CO-deficient rhodium hydrogenation catalyst and the gas comprises hydrogen and carbon monoxide, wherein the reaction of the CO-deficient rhodium hydrogenation catalyst with the gas affords a hydrogenation-active rhodium hydrogenation catalyst.

The reaction product of the preforming which comprises the hydrogenation-active rhodium hydrogenation catalyst may then be supplied to an asymmetric hydrogenation reaction together with a substrate to be hydrogenated to afford a hydrogenation reaction mixture. After separation of the hydrogenation product the residue comprising CO-deficient rhodium hydrogenation catalyst is returned to the preforming. The hydrogenation product may be separated from the hydrogenation mixture by processes known per se to those skilled in the art, for example by distillation and/or flash evaporation, wherein the hydrogenation-active rhodium hydrogenation catalyst loses CO and a CO-deficient rhodium hydrogenation catalyst remains.

In one embodiment the substrate to be hydrogenated is cis-citral. The hydrogenation product of cis-citral is R-citronellal.

The employed rhodium catalysts comprise at least one CO ligand at least in a form appearing in the catalyst cycle or in a precursor form preceding the actual catalyst cycle, it being immaterial whether this catalyst form comprising at least one CO ligand constitutes the actual catalytically active catalyst form. In order to stabilize the catalyst forms comprising CO ligands it may be advantageous to additionally supply carbon monoxide to the reaction mixture during the hydrogenation.

The rhodium catalyst typically comprises at least one optically active ligand. Such catalysts are obtainable for example by reaction of a suitable rhodium compound soluble in the hydrogenation mixture and having an optically active ligand comprising at least one phosphorus and/or arsenic atom.

Examples of employable rhodium compounds are: $RhCl_3$, $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$, $Rh_6(CO)_{16}$, wherein "acac" stands for acetylacetonate and "cod" stands for a cyclooctadiene ligand.

The recited rhodium compounds are contacted with a further compound which is optically active, preferably substantially enantiomerically pure (i.e. having an enantiomeric excess of at least about 99%), and comprises at least one phosphorus and/or arsenic atom, preferably at least one phosphorus atom. This compound, which is to be referred to as a chiral ligand, forms the rhodium catalyst together with the employed rhodium compound.

Chiral ligands which comprise two phosphorus atoms and form chelate complexes with rhodium are especially preferred.

Chiral ligands suitable in the context of the present invention include compounds such as are described for example in: I. Ojima (ed.), Catalytic Asymmetric Synthesis, Wiley-VCh, 2nd edition, 2000 or in E. N. Jacobsen, A. Pfaltz, H. Yamamoto (ed.), Comprehensive Asymmetric Catalysis, 2000, Springer or in W. Tang, X. Zhang, Chem. Rev. 2003, 103, 3029-3069.

Preferred ligands are chiral bidentate biphosphine ligands, especially those of general formulae (I) to (III)

wherein
$R^5$, $R^6$ each independently of one another represent an unbranched, branched or cyclic hydrocarbon radical having 1 to 20 carbon atoms which is saturated or may comprise one or more, generally 1 to about 4, nonconjugated ethylenic double bonds and which is unsubstituted or bears one or more, generally 1 to 4, identical or different substituents selected from $OR^{13}$, $NR^{14}R^{15}$, halogen, $C_6$-$C_{10}$-aryl and $C_3$-$C_9$-hetaryl, or $R^5$ and $R^6$ may jointly represent a 2- to 10-membered alkylene group or a 3- to 10-membered cycloalkylene group, wherein 1, 2, 3 or 4 nonadjacent CH groups may be replaced by 0 or N—$R^{13}$, wherein the alkylene group and the cycloalkylene group are saturated or comprise one or two nonconjugated ethylenic double bonds and wherein the alkylene group and the cycloalkylene group are unsubstituted or bear one or more identical or different substituents selected from $C_1$-$C_4$-alkyl;

$R^7$, $R^8$ each independently of one another represent hydrogen or straight-chain or branched $C_1$-$C_4$-alkyl and $R^9$, $R^{10}$, $R^{11}$, $R^{12}$ are identical or different and represent $C_6$-$C_{10}$-aryl which is unsubstituted or bears one or more substituents selected from $C_1$-$C_6$-alkyl, $C_3$-$C_6$-cycloalkyl, $C_6$-$C_{10}$-aryl, $C_1$-$C_6$-alkoxy and amino;

$R^{13}$, $R^{14}$, $R^{15}$ each independently of one another represent hydrogen, $C_1$-$C_4$-alkyl, $C_6$-$C_{10}$-aryl, $C_7$-$C_{12}$-aralkyl or $C_7$-$C_{12}$-alkylaryl, wherein $R^{14}$ and $R^{15}$ may also jointly represent an alkylene chain having 2 to 5 carbon atoms which may be interrupted by N or O.

With regard to the formulae (I), (II) and (III) the variables are especially defined as follows:

$R^5$, $R^6$ each independently of one another represent $C_1$-$C_4$-alkyl or $R^5$ and $R^6$ jointly represent a $C_3$-$C_5$-alkanediyl radical $C_3$-$C_7$-alkenediyl radical, $C_5$-$C_7$-cycloalkanediyl radical or a $C_5$-$C_7$-cycloalkenediyl radical, wherein the four above-mentioned radicals are unsubstituted or bear one or more identical or different substituents selected from $C_1$-$C_4$-alkyl;

$R^7$, $R^8$ each independently of one another represent hydrogen or $C_1$-$C_4$-alkyl;

$R^9$, $R^{10}$, $R^{11}$, $R^{12}$ each represent phenyl.

Chiral, bidentate biphosphine ligands particularly preferred on account of being readily available are compounds obtainable under the designation "chiraphos" and having the formula:

The chiral ligands are advantageously employed in an amount of about 0.9 to about 10 mol, preferably about 1 to about 4 mol, per mol of employed rhodium compound. The optically active rhodium catalyst is suitably generated in situ by reaction of an achiral rhodium compound with a chiral, bidentate biphosphine ligand. In this context the term "in-situ" is to be understood as meaning that the catalyst is generated immediately before hydrogenation.

It has been found that the presence of monodentate ligands can increase the activity of the catalyst. In a preferred embodiment of the process according to the invention compounds of formula (IV)

are employed, for example in the liquid introduced into the reactor, wherein Z in formula (IV) represents a $CHR^{18}R^{19}$ group and wherein the variables $R^{16}$, $R^{17}$, $R^{18}$, $R^{19}$ independently of one another and especially jointly are defined as follows:

$R^{16}$, $R^{17}$: are identical or different and represent phenyl which is unsubstituted or bears 1, 2 or 3 substituents selected from methyl and methoxy, wherein $R^{16}$ and $R^{17}$ each especially represent unsubstituted phenyl;

$R^{18}$ represents $C_1$- to $C_4$-alkyl, especially methyl;

$R^{19}$ represents $C_1$- to $C_4$-alkyl bearing a $P(=O)R^{19a}R^{19b}$ group and especially a $CH_2$—$P(=O)R^{19a}R^{19b}$ or $CH(CH_3)$—$P(=O)R^{19a}R^{19b}$ group;

wherein $R^{19a}$, $R^{19b}$: are identical or different and represent phenyl which is unsubstituted or bears 1, 2 or 3 substituents selected from methyl and methoxy, wherein particularly preferably $R^{19a}$ and $R^{19b}$ each represent unsubstituted phenyl.

In this preferred embodiment of the process according to the invention it is particularly preferable to employ a compound of formula (IV), wherein $R^{16}$, $R^{17}$: represent unsubstituted phenyl;

$R^{18}$ represents methyl;

$R^{19}$ represents a $CH(CH_3)$—$P(=O)R^{19a}R^{19b}$ group, wherein $R^{19a}$ and $R^{19b}$ each represent unsubstituted phenyl.

This is the compound (2-(diphenylphosphoryl)-1-methylpropyl)diphenylphosphane (chiraphos monoxide) including the (R,R) enantiomer (=(R,R)-chiraphos monoxide) and the (S,S) enantiomer (=(S,S)-chiraphos monoxide) and mixtures of (R,R)-chiraphos monoxide and (S,S)-chiraphos monoxide.

When the radicals $R^{18}$ and $R^{19}$ in general formula (IV) are different, the carbon atom bearing the radicals $R^{18}$ and $R^{19}$ may have an (R) or (S) configuration. These compounds of general formula (IV) may be in the form of pure (R) or pure (S) stereoisomers or as mixtures thereof. Generally employed in these cases are the pure (R) and (S) stereoisomers but any stereoisomer mixtures are also suitable for use in the present process.

A pure stereoisomer is here and hereinbelow to be understood as meaning chiral substances which in terms of the desired stereoisomer have an enantiomeric excess (ee) of at least 80% ee, in particular at least 90% ee and especially at least 95% ee.

In particular, the chiral ligand employed is chiraphos and the monodentate binding compound employed is (2-(diphenylphosphoryl)-1-methylpropyl)diphenylphosphane (chiraphos monoxide). By way of example, the chiral ligand employed is R-chiraphos and the monodentate binding compound employed is (R,R)-chiraphos monoxide and/or (S,S)-chiraphos monoxide. Alternatively, the chiral ligand employed is S-chiraphos and the monodentate binding compound employed is (R,R)-chiraphos monoxide and/or (S,S)-chiraphos monoxide.

According to the invention the compound of formula (IV) is generally employed in an amount of 0.01 to 1 mol, preferably 0.02 to 0.8 mol, particularly preferably 0.03 to 0.7 mol and especially in an amount of 0.04 to 0.6 mol per mol of rhodium.

Further embodiments of the hydrogenation catalyst and of the monodentate ligand are described in US 2018/0057437 A1, WO 2006/040096 A1 and WO 2008/132057 A1.

Preforming the rhodium catalyst typically comprises dissolving the selected rhodium compound and the selected chiral ligand in a suitable solvent/dissolution medium inert under the reaction conditions such as for example ether, tetrahydrofuran, methyltetrahydrofuran, toluene, xylenes, chlorobenzene, octadecanol, biphenyl ether, Texanol, Marlotherm, Oxoöl 9N (hydroformylation products of isomeric octenes, BASF Aktiengeselschaft), citronellal and the like. Employable dissolution media may also include the hydrogenation product or any high-boiling byproducts generated during the conversion. In the reactor according to the invention the resulting solution is typically pressurized with a gas mixture comprising hydrogen and carbon monoxide at a pressure of typically about 5 to about 350 bar, preferably of about 20 to about 200 bar and particularly preferably of about 50 to about 100 bar. Preforming preferably employs a gas mixture comprising about 30 to 99 vol % of hydrogen,
1 to 70 vol % of carbon monoxide and
0 to 5 vol % of further gases, wherein the reported amounts in vol % sum to 100 vol %.

A gas mixture especially preferred for preforming is so-called synthesis gas which typically comprises about 35 to 55 vol % of carbon monoxide in addition to hydrogen and traces of further gases.

The preforming of the catalyst is typically performed at temperatures of about 25° C. to about 100° C., preferably at about 40° C. to about 80° C. The preforming is typically completed after about 1 h to about 24 h, often after about 1 to about 12 h. Preforming is preferably followed by asymmetric hydrogenation of a selected substrate. After the preceding preforming the selected substrate may generally be successfully performed with or without supplying additional carbon monoxide. It is advantageous when a preforming is performed as described and additional carbon monoxide is added to the reaction mixture during the asymmetric hydrogenation.

In this embodiment the recited preforming of the catalyst precursor stage is performed at a pressure of 5 to 100 bar with a gas mixture comprising 20 to 90 vol % of carbon monoxide, 10 to 80 vol % of hydrogen and 0 to 5 vol % of further gases, wherein the recited volume fractions sum to 100 vol %. In addition, excess carbon monoxide is separated from the thus-obtained catalyst before use in the asymmetric hydrogenation. The term excess carbon monoxide is to be understood as meaning carbon monoxide present in the obtained reaction mixture in gaseous or dissolved form and not bonded to the rhodium catalyst/its precursor. The excess carbon monoxide not bonded to the catalyst is thus at least largely removed, i.e. to such an extent that any residual amounts of dissolved carbon monoxide do not have a disruptive effect in the subsequent hydrogenation. This is typically ensured when about 90%, preferably about 95% or more, of the carbon monoxide employed for preforming is separated. The excess carbon monoxide is preferably completely removed from the catalyst obtained by preforming.

The separation of the excess carbon monoxide from the obtained catalyst/from the reaction mixture comprising the catalyst may be effected in various ways. The catalyst/the mixture comprising the catalyst obtained by preforming is preferably decompressed to a pressure of up to about 5 bar (absolute), preferably, especially when performing the preforming in the pressure range from 5 to 10 bar, to a pressure of less than 5 bar (absolute), preferably to a pressure in the range from about 1 to about 5 bar, preferably 1 to less than 5 bar, particularly preferably to a pressure in the range from 1 to 3 bar, very particularly preferably to a pressure in the range from about 1 to about 2 bar, especially preferably to standard pressure, so that gaseous, unbonded carbon monoxide escapes from the product of the preforming. The abovementioned decompression of the preformed catalyst may be carried out for example using a high-pressure separator such as is known per se to those skilled in the art. Such separators in which the liquid is in the continuous phase are described for example in: Perry's Chemical Engineers' Handbook, 1997, 7th ed., McGraw-Hill, pp. 14.95 and 14.96; prevention of possible droplet entrainment is described on pages 14.87 to 14.90. Decompression of the preformed catalyst may be carried out in one or two stages until achievement of the desired pressure in the range from 1 bar to about 5 bar, wherein the temperature typically falls to 10° C. to 40° C. Separation of excess carbon monoxide may alternatively be effected by so-called stripping of the catalyst/the mixture comprising the catalyst with a gas, advantageously with a gas which is inert under the reaction conditions. The term stripping is understood by those skilled in the art to mean introduction of a gas into the catalyst/the reaction mixture comprising the catalyst such as is described for example in W. R. A. Vauck, H. A. Müller, Grundoperationen chemischer Verfahrenstechnik [Basic Operations in Chemical Process Technology], Deutscher Verlag für Grundstoffchemie Leipzig, Stuttgart, 10th edition, 1984, page 800. Examples of inert gases suitable therefor include: hydrogen, helium, neon, argon, xenon, nitrogen and/or CO2, preferably hydrogen, nitrogen, argon.

If carbon monoxide is supplied to the reaction system the supplying may be undertaken in various ways. Thus for example the carbon monoxide may be admixed with the hydrogen used for asymmetric hydrogenation or else directly metered into the reaction solution in gaseous form. The carbon monoxide is preferably admixed with the hydrogen used for asymmetric hydrogenation.

The asymmetric hydrogenation is preferably performed with hydrogen having a carbon monoxide content in the range from 50 to 3000 ppm, in particular in the range from 100 to 2000 ppm, especially in the range from 200 to 1000 ppm and very especially in the range from 400 to 800 ppm.

The hydrogenation product may be separated from the hydrogenation mixture by processes known per se to those skilled in the art such as for example by distillation and/or flash evaporation and the remaining catalyst utilized in the context of further conversions. In the context of the preferred embodiment it is advantageous to eschew addition of solvents and perform the recited conversions in the substrate to be converted/the product and optionally in high-boiling byproducts as the dissolution medium. Special preference is given to a continuous reaction mode with reuse/recycling of the homogeneous catalyst stabilized according to the invention.

In a preferred embodiment a prochiral α,β-unsaturated carbonyl compound is hydrogenated. A prochiral α, β-unsaturated carbonyl compound can form a chirality center by addition reaction at the olefinic double bond. To this end the double bond bears four different substituents. The prochiral α, β-unsaturated carbonyl compound is preferably selected from compounds of general formula (V)

(V)

wherein
$R^1$, $R^2$ are distinct from one another and each represent an unbranched, branched or cyclic hydrocarbon radical having 1 to 25 carbon atoms which is saturated or comprises one or more, nonconjugated ethylenic double bonds and which is unsubstituted or bears one or more identical or different substituents selected from $OR^4$, $NR^{5a}R^{5b}$, halogen, $C_6$-$C_{10}$-aryl and hetaryl having 5 to 10 ring atoms, $R^3$ represents hydrogen or an unbranched, branched or cyclic hydrocarbon radical having 1 to 25 carbon atoms which is saturated or comprises one or more, nonconjugated ethylenic double bonds and which is unsubstituted or bears one or more identical or different substituents selected from $OR^4$, $NR^{5a}R^{5b}$, halogen, $C_6$-$C_{10}$-aryl and hetaryl having 5 to 10 ring atoms, or $R^3$ jointly with either of the radicals $R^1$ and $R^2$ may also represent a 3- to 25-membered alkylene group wherein 1, 2, 3 or 4 nonadjacent $CH_2$-groups may be replaced by O or N—$R^{5c}$, wherein the alkylene group is saturated or comprises one or more nonconjugated ethylenic double bonds and wherein the alkylene group is unsubstituted or bears one or more identical or different substituents selected from $OR^4$, $NR^{5a}R^{5b}$, halogen, $C_1$-$C_4$-alkyl, $C_6$-$C_{10}$-aryl and hetaryl having 5 to 10 ring atoms, wherein two substituents may also jointly represent a 2- to 10-membered alkylene group, wherein the 2- to 10-membered alkylene group is saturated or comprises one or more non-conjugated ethylenic double bonds and wherein the 2- to 10-membered alkylene group is unsubstituted or bears one or more identical or different substituents selected from $OR^4$, $NR^{5a}R^{5b}$, halogen, $C_6$-$C_{10}$-aryl and hetaryl having 5 to 10 ring atoms;

wherein
$R^4$ represents hydrogen, $C_1$-$C_6$-alkyl, $C_6$-$C_{10}$-aryl, $C_6$-$C_{14}$-aryl-$C_1$-$C_{10}$-alkyl, or $C_1$-$C_{10}$-alkyl-$C_6$-$C_{14}$-aryl;

$R^{5a}$, $R^{5b}$ each independently of one another represent hydrogen, $C_1$-$C_6$-alkyl, $C_6$-$C_{10}$-aryl, $C_6$-$C_{14}$-aryl-$C_1$-$C_{10}$-alkyl or $C_1$-$C_{10}$-alkyl-$C_6$-$C_{14}$-aryl or

$R^{5a}$ and $R^{5b}$ may also jointly represent an alkylene chain having 2 to 5 carbon atoms which may be interrupted by N or O; and $R^{5c}$ represents hydrogen, $C_1$-$C_6$-alkyl, $C_6$-$C_{10}$-aryl, $C_6$-$C_{14}$-aryl-$C_1$-$C_{10}$-alkyl, or $C_1$-$C_{10}$-alkyl-$C_6$-$C_{14}$-aryl.

In preferred embodiments the prochiral α,β-unsaturated carbonyl compound is selected from compounds of general formulae (Va) and (Vb)

(Va)

(Vb)

wherein
$R^1$, $R^2$ each represent an unbranched or branched hydrocarbon radical having 2 to 25 carbon atoms which is saturated or comprises 1, 2, 3, 4 or 5 nonconjugated ethylenic double bonds.

A particularly preferred embodiment relates to a process for producing optically active citronellal of formula (VI)

(VI)

wherein * denotes the asymmetric center;
by asymmetric hydrogenation of geranial of formula (Va-1) or of neral of formula (Vb-1)

(Va-1)

(Vb-1)

or a mixture comprising neral and geranial. A mixture comprising neral and geranial is known as citral.

The thus-obtainable optically active citronellal of formula (VI) may be subjected to a cyclization to afford optically active isopulegol and the optically active isopulegol hydrogenated to afford optically active menthol.

The invention further provides a process for adapting the reaction volume of a reactor suitable for performing a gas/liquid biphasic high-pressure reaction in which an internal element is arranged such that a cavity open at the bottom is formed.

In a preferred embodiment the internal element is an internal element in accordance with the above-described third internal element including the embodiments described in connection therewith.

The invention is more particularly elucidated by the accompanying figures.

FIG. 1

Figure 1:
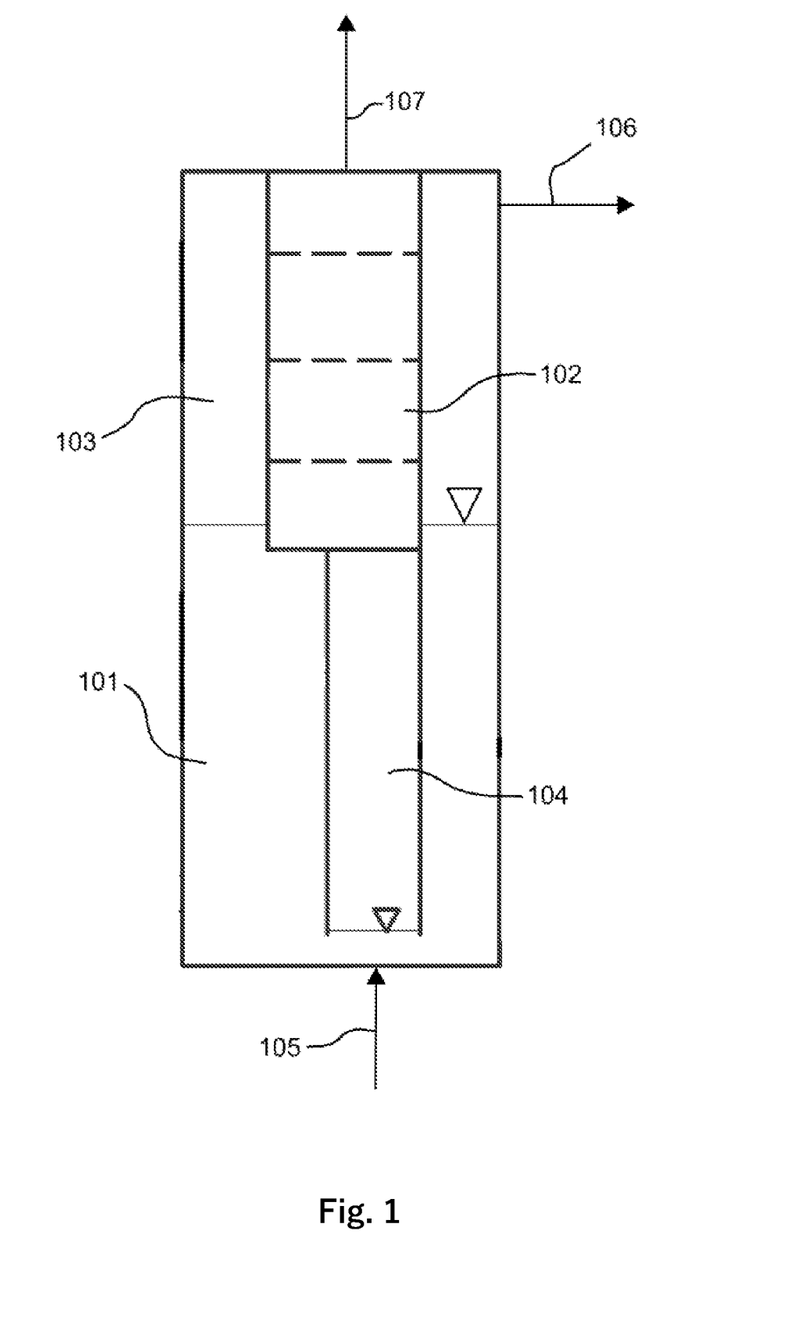
FIG. 1 shows a schematic diagram of a reactor suitable for performing the process according to the invention.

The reactor comprises a backmixed zone 101, a zone of limited backmixing 102 whose backmixing is limited by internal trays, a gas space 103 and a cavity 104. An injection nozzle (not shown) is used to supply a gas and a liquid from the conduit 105 to the backmixed zone 101.

The backmixed zone 101 has a gas outlet 106 through which unconverted gas is discharged. Liquid ascends from the backmixed zone 101 via a liquid passage (not shown) into the zone of limited backmixing 102. Reaction product is discharged via the reaction product outlet 107.

FIG. 2

Figure 2:
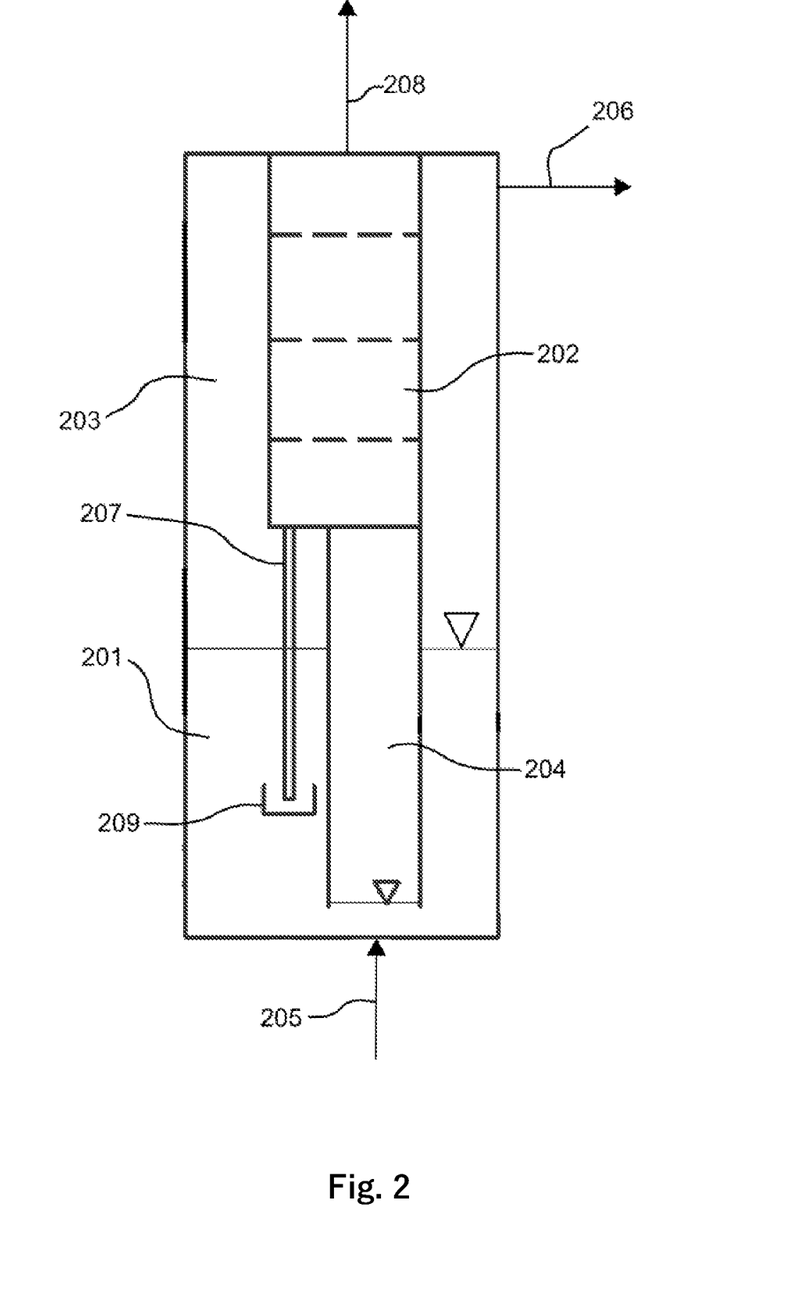
FIG. 2 shows a schematic diagram of a reactor suitable for performing the process according to the invention.

The reactor comprises a backmixed zone 201, a zone of limited backmixing 202 whose backmixing is limited by internal trays, a gas space 203 and a cavity 204. An injection nozzle (not shown) is used to supply a gas and a liquid from the conduit 205 to the backmixed zone 201.

The backmixed zone 201 has a gas outlet 206 through which unconverted gas is discharged. Liquid ascends from the backmixed zone 201 into the zone of limited backmixing 202 via the riser tube 207 whose lower end is arranged below the liquid level. Reaction product is discharged via the reaction product outlet 108. The reactor comprises a deflection weir 209 which substantially prevents entry of gas into the riser tube 207.

The invention claimed is:

1. A process for performing a continuous gas/liquid biphasic high-pressure reaction, comprising introducing a gas and a liquid into a backmixed zone of a reactor and dispersing the gas in the liquid in the backmixed zone by stirring, injection of gas and/or a liquid jet, wherein a reaction mixture consecutively traverses the backmixed zone and a zone of limited backmixing, and withdrawing a liquid reaction product at a reaction product outlet of the zone of limited backmixing, wherein the reactor comprises:

an interior formed by a cylindrical vertically oriented elongate shell, a bottom and a cap, wherein the interior is divided by means of internals into the backmixed zone, the zone of limited backmixing and a cavity, a first cylindrical internal element which in the interior extends in the longitudinal direction of the reactor and which delimits the zone of limited backmixing from the backmixed zone, backmixing-preventing second internal elements in the form of random packings, structured packings or liquid-permeable trays arranged in the zone of limited backmixing and a third internal element which in the interior extends in the longitudinal direction of the reactor and is open at the bottom, wherein the third internal element forms the cavity in which gas bubbles collect and do not escape upwards, thus preventing the volume of the cavity from being occupied by liquid and reducing the reaction volume.

2. The process according to claim 1, wherein gas is injected via a two-fluid nozzle.

3. The process according to claim 1, wherein the third internal element has a fluid outlet by means of which the gas volume in the cavity may be adjusted.

4. The process according to claim 1, wherein the volume ratio of the backmixed zone to the zone of limited backmixing is in the range from 0.25:1 to 4:1.

5. The process according to claim 1, wherein the volume ratio of the backmixed zone to the cavity is in the range from 0.5:1 to 10:1.

6. The process according to claim 1, wherein the first internal element is arranged concentrically to the shell so that the zone of limited backmixing has a circular horizontal cross section.

7. The process according to claim 1, wherein the reactor comprises at least one fourth internal element which is arranged in the gas space and has a surface which promotes coalescence of foaming media.

8. The process according to claim 1, wherein the reactor comprises a riser tube whose lower end is arranged within the backmixed zone and whose upper end opens into the zone of limited backmixing so that liquid from the backmixed zone can ascend into the zone of limited backmixing via the riser tube.

9. The process according to claim 1 for preforming a homogeneous rhodium hydrogenation catalyst comprising at least one CO ligand, wherein the liquid comprises a dissolved CO-deficient rhodium hydrogenation catalyst and wherein the gas comprises hydrogen and carbon monoxide, wherein the reaction of the CO-deficient rhodium hydrogenation catalyst with the gas affords a hydrogenation-active rhodium hydrogenation catalyst.

10. The process according to claim 9, wherein the CO-deficient rhodium hydrogenation catalyst comprises at least one chiral ligand, in particular chiraphos.

11. The process according to claim 9, wherein the liquid comprises a compound of formula (IV)

(IV)

wherein Z in formula (IV) represents a CHR³R⁴ group and wherein the variables R¹, R², R³, R⁴ independently of one another are defined as follows:
R¹, R²: are identical or different and represent phenyl which is unsubstituted or bears 1, 2, or 3 substituents selected from methyl and methoxy;
R³ represents C₁- to C₄-alkyl, especially methyl;
R⁴ represents C₁- to C₄-alkyl bearing a P(=O)R⁴ᵃR⁴ᵇ group;
wherein
R⁴ᵃ, R⁴ᵇ: are identical or different and represent phenyl which is unsubstituted or bears 1, 2 or 3 substituents selected from methyl and methoxy.

12. The process according to claim 9, wherein the reaction product of the preforming is supplied to an asymmetric hydrogenation reaction together with a substrate to be hydrogenated to afford a hydrogenation reaction mixture and a hydrogenation product is separated from the hydrogenation reaction mixture to afford a residue comprising CO-deficient rhodium hydrogenation catalyst which is returned to the preforming.

13. A process for producing optically active menthol in which optically active citronellal of formula (VI)

(VI)

wherein * denotes the asymmetric center;
is produced by the process according to claim 12, wherein the hydrogenation reaction comprises the asymmetric hydrogenation of geranial of formula (Va-1) or of neral of formula (Vb-1)

(Va-1)

(Vb-1)

or a mixture comprising neral and geranial,
the optically active citronellal of formula (VI) is subjected to a cyclization to afford optically active isopulegol and the optically active isopulegol is hydrogenated to afford optically active menthol.

14. A process for adapting the reaction volume of a reactor suitable for performing a gas/liquid biphasic high-pressure reaction having an outlet for a liquid reaction product in which an internal element is arranged so as to form a cavity open at the bottom in which gas bubbles collect and do not escape upwards, thus preventing the volume of the cavity from being occupied by liquid and reducing the reaction volume.

15. The process according to claim 9, wherein the liquid comprises a compound of formula (IV)

(IV)

wherein Z in formula (IV) represents a CHR³R⁴ group and wherein the variables R¹, R², R³, R⁴ independently of one another and especially jointly are defined as follows:
R¹, R²: are each unsubstituted phenyl;
R³ represents methyl;
R⁴ represents a CH₂—P(=O)R⁴ᵃR⁴ᵇ or CH(CH₃)—P(=O)R⁴ᵃR⁴ᵇ group;
wherein
R⁴ᵃ, R⁴ᵇ: are each unsubstituted phenyl.

* * * * *